United States Patent [19]

Fukuda et al.

[11] 4,259,965

[45] Apr. 7, 1981

[54] SKIN ELECTRODE

[75] Inventors: Kotaro Fukuda, Tokyo; Yosinori Okamoto, Fujimi; Masakatsu Shimada, Iwatsuki; Toshiaki Kato; Katsuhiko Tabuchi, both of Chiba; Makoto Shimura, Yokosuka; Takashi Fujiwara, Nagareyama, all of Japan

[73] Assignee: TDK Electronics Co., Ltd., Tokyo, Japan

[21] Appl. No.: 23,287

[22] Filed: Mar. 23, 1979

[30] Foreign Application Priority Data

Mar. 29, 1978 [JP] Japan .............................. 53-40562[U]

[51] Int. Cl.³ .............................................. A61B 5/04
[52] U.S. Cl. .................................................... 128/640
[58] Field of Search ............................... 128/639–641, 128/642, 644, 798, 802, 803

[56] References Cited

U.S. PATENT DOCUMENTS

| | | | |
|---|---|---|---|
| 3,964,470 | 6/1976 | Trombley | 128/642 |
| 4,051,842 | 10/1977 | Hazel et al. | 128/640 |
| 4,067,342 | 1/1978 | Burton | 128/798 |
| 4,112,941 | 9/1978 | Larimore | 128/641 |
| 4,166,453 | 9/1979 | McClelland | 128/639 |

*Primary Examiner*—Lee S. Cohen
*Attorney, Agent, or Firm*—Burgess, Ryan and Wayne

[57] ABSTRACT

In a skin electrode for connecting monitoring equipment to the surface of the skin which is separable into two assemblies: a base assembly adapted to be mounted to the surface of the skin and having a sensing element, and; a terminal assembly adapted to be releasably coupled with the base assembly and having a lead for connection to the monitoring equipment, an improvement wherein the terminal assembly is provided with a magnet while the base assembly is provided with a ferromagnetic element, whereby the releasable coupling and electrical connection of the assemblies may be ensured by the action of the magnet.

4 Claims, 12 Drawing Figures

SKIN ELECTRODE

BACKGROUND OF THE INVENTION

The present invention relates to a skin electrode for diagnostic purposes. More particularly, it relates to an improvement of a skin electrode for operatively connecting monitoring equipment to the surface of the skin to be monitored which is separable into two assemblies; a base assembly adapted to be mounted to the surface of the skin and having a sensing element for detecting biopotentials from the surface of the skin and transforming them into electrical signals, and; a terminal assembly adapted to be releasably coupled with the base assembly and having a lead for connection to the monitoring equipment for the transmission of the electrical signals.

When organs or tissues of a living body are excited, weak biopotentials are created. It is a widely known practice to transform such biopotentials into electrical signals which are monitored for diagnostic purposes by means of instruments, such as electrocardiographs and electroencephalographs. As the biopotentials are very weak, for example, on the order of 2 millivolts, the state of contact between the surface of the skin to be monitored and the sensing element significantly affects the readout results and, if it is not appropriate, unacceptable errors are invited. Accordingly, it is a usual practice to apply an electrolyte gel between the sensing element of the skin electrode and the surface of the skin so as to reduce contact resistance between them and to minimize variations in the accuracy of the electrode readout.

Known is a skin electrode comprising: a base assembly adapted to be mounted to the surface of the skin to be monitored and having a sensing element for detecting biopotentials from the surface of the skin and transforming them into electrical signals, and; a terminal assembly adapted to be releasably coupled with the base assembly and having a lead for connection to the monitoring equipment for the transmission of the electrical signals. For electrical connection of the base and terminal assemblies together, use has heretofore been made of a jack-plug, clip, of snap-hook type connection. Typically, the base assembly includes a male connector adapted to be snapped into a female connector provided in the terminal assembly. The force required for snapping into place such male and female connectors often causes the electrolyte gel applied between the base assembly and the surface of skin to leak out from the skin area to be monitored. Such leaking-out of the gel invites the following inconveniences.

(1) The effective area of the surface of the skin from which biopotentials are taken out varies.

(2) The effective site of the skin is displaced and, thus, the accuracy of signals is lowered.

(3) The base assembly normally includes a flexible plastic disc having a side toward the surface of the skin coated with a pressure-sensitive adhesive, by which the base assembly may be securely mounted to the surface of the skin. If the electrolyte gel is forced to be present between the disc and the surface of skin, the adhesion eventually becomes so poor that the secure mounting of the base assembly to the surface of skin is not ensured.

(4) If the electrolyte gel which has leaked out comes into contact with undesired parts of the base assembly, the signals transmitted to the monitoring equipment include perturbations resulting in misdiagnosis.

Thus, with such prior art skin electrodes, the connection of the base and terminal assemblies can only be safely performed by a person well trained in that operation.

SUMMARY OF THE INVENTION

An object of the invention is to provide a skin electrode of a thin simple structure capable of being readily fabricated, which electrode is improved over those of the prior art in that the connection of the base and terminal assemblies can easily be performed even by a non-trained person without the leaking-out of the electrolyte gel and other associated inconveniences.

The above-mentioned object can be attained by employing a magnet in the terminal assembly and a ferromagnetic element in the base assembly in the manner as proposed herein.

Thus, the invention provides an improvement in a skin electrode for operatively connecting monitoring equipment to the surface of the skin to be monitored comprising:

a base assembly adapted to be mounted to the surface of the skin comprising:
  a disc-shaped sensing element for detecting biopotentials from the surface of skin and transforming them into electrical signals;
  a disc-shaped ferromagnetic element in electrical contact with and superimposed on the sensing element with the latter element located near the skin;
  a cylindrical tubular case formed of an insulating plastics material for holding the sensing and ferromagnetic elements in place in the middle of a cylindrical tubular body of the case so that a first cylindrical chamber is defined on one side of the ferromagnetic element remote from the skin and a second cylindrical chamber is defined on one side of the sensing element near the skin, the case having an outwardly extending flange at that end of its cylindrical tubular body near the skin;
means for securing the case to the surface of the skin;
and a terminal assembly adapted to be releasably coupled with the base assembly comprising:
a disc-shaped magnet;
a cylindrical yoke formed of a ferromagnetic substance having a depression opened toward the skin where the magnet is held in place, the outer diameter of the yoke being slightly smaller than the inner diameter of the first cylindrical chamber of the base assembly, so that the yoke may fit into the first cylindrical chamber to form a coupling of the assemblies;
a lead connected to the yoke for connection to the monitoring equipment for the transmission of the electrical signals; and
a circular cover member, which holds the yoke in place and through which the lead is allowed to pass.

The means for securing the case to the surface of the skin comprises a centrally apertured disc formed of a flexible material situated upon the flange of the case with the tubular body of the case inserted into the aperture, a layer of a pressure-sensitive adhesive applied to the surface facing the skin of the portion of the centrally apertured disc extending beyond the flange of the case, and a removable backing strip disposed on the layer of the pressure-sensitive adhesive to protect the stickiness of the pressure-sensitive adhesive prior to use.

The circular cover member may be adhesively fixed on that flat surface of the cylindrical yoke remote from the skin. Alternatively, the cylindrical yoke may be provided with a flange extending perpendicularly to its axis adapted to be mechanically engaged with a peripheral end portion of the circular cover member.

The cylindrical tubular case of the base assembly may have an inwardly extending annular rim at that end of its cylindrical tubular body remote from the skin, and the ferromagnetic element may be held in abutting engagement with the side of the annular rim near the skin so that the first cylindrical chamber may be defined on that side of the ferromagnetic element remote from the skin by the inner surface of the annular rim. Alternatively, the cylindrical tubular case of the base assembly may have an inwardly extending annular rim at that end of its cylindrical tubular body near the skin, and the sensing element may be held in abutting engagement with that side of the annular rim remote from the skin so that the second cylindrical chamber is defined on that side of the sensing element near the skin by the inner surface of the annular rim.

DETAILED DESCRIPTION OF THE PREFERRED EMBODIMENTS OF THE INVENTION

Figure 1A:
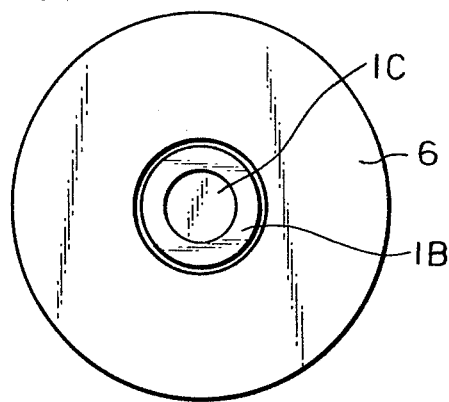
FIGS. 1(a), (b) and (c) are respectively top plan, side elevational cross-sectional and bottom plan views, illustrating one example of a base assembly of the skin electrode in accordance with the invention.
Figure 1B:
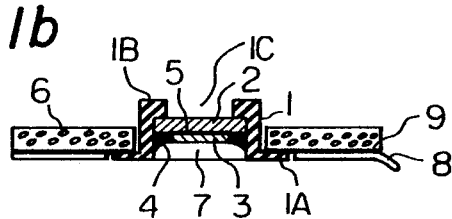
Figure 1C:
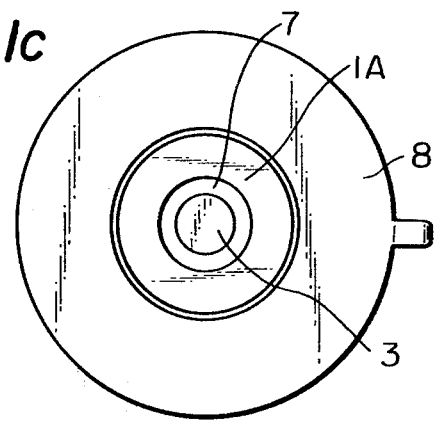

Referring to FIGS. 1(a), (b) and (c), the illustrated base assembly comprises a case 1 for holding a ferromagnetic element 2 and a sensing element 3 in place. The case 1 is formed of an insulating rigid plastic material such as polyethylene or polypropylene. It comprises a cylindrical tube of a small height, generally less than 4 mm, with an outwardly extending flange 1A at the bottom and an inwardly extending rim 1B on the top. The ferromagnetic element 2 comprises a flat disc formed of a steel having a high density of saturated magnetic flux and a high electrical conductivity, and is inserted into the case 1 from the bottom into abutting engagement with the underside of the rim 1B. The inner surface of the annular rim 1B and the upper surface of the ferromagnetic element 2 define an upwardly opened cylindrical chamber 1C for receiving a part of the terminal assembly as described hereinafter. The sensing element 3 which comprises a flat disc formed of a suitable sensing substance such as silver is also inserted into the case 1 from the bottom until it comes into electrical contact with the underside of the ferromagnetic element 3. The ferromagnetic element 2 and sensing element 3 are held in place in the case 1 by means of an adhesive 4. Between the ferromagnetic and sensing elements, there is placed a suitable conductive paste 5 (or springs) so as to avoid variations in the contact resistance between them which will otherwise vary from product to product due to unavoidable variations in the products. Any space between the case 1 and the elements 2 and 3 should be desirably filled with a suitable insulating resin. The base assembly further comprises a centrally apertured disc 6 formed of foam plastics, paper or cloth. The member 6 rests on the flange 1A of the case 1 with the cylindrical body inserted into the aperture. The underside of the assembly is coated with a suitable pressure-sensitive adhesive 9 so that the assembly may be adhesively secured to the surface of the skin under observation. A removable backing strip 8 is disposed on the layer of the pressure-sensitive adhesive to protect the stickiness of the adhesive prior to use.

Upon securing the base assembly on the surface of the skin, electrolyte gel may be placed between the sensing element 3 and the surface of the skin by one of the following methods.

(1) A pad of sponge fabricated in a suitable shape and impregnated with the electrolyte gel is placed in a cavity 7 defined by the lower surface of the sensing element 3 and the inner surface of the lower portion of cylindrical body of the case 1.

(2) A pad of sponge fabricated in a suitable shape and placed in the cavity 7 is impregnated with the electrolyte gel.

(3) The electrolyte gel is injected into the cavity 7.

Figure 2A:
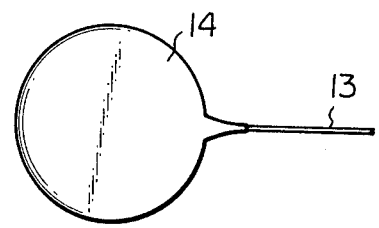
FIGS. 2(a), (b) and (c) are respectively top plan, side elevational cross-sectional and bottom plan views, illustrating one example of a terminal assembly of the skin electrode in accordance with the invention.
Figure 2B:
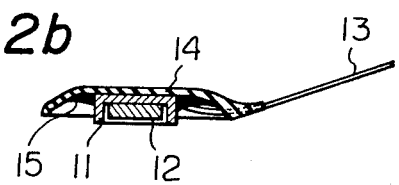
Figure 2C:
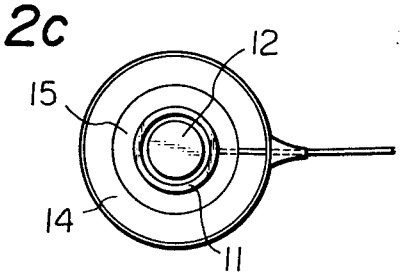

The terminal assembly illustrated in FIGS. 2(a), (b) and (c) comprises a yoke 11, a magnet 12, a lead 13 and a cover member 14. The yoke 11 is formed of a ferromagnetic substance, such as a steel, and is in the shape of a cylinder of a small height having a downwardly opened depression at the bottom where the magnet disc 12 is held in place. Thus, the yoke 11 serves not only to hold the magnet in place but also to orient the magnetic flux from the magnet 12. The outer diameter of the cylindrical yoke is slightly smaller than the inner diameter of the cylindrical chamber 1C of the base assembly, whereby the yoke 11 holding the magnet of the terminal assembly may fit into the chamber 1C of the base assembly to form a coupling of the assemblies. One end of the lead 13 is connected to the outer cylindrical surface of the yoke, for example, by soldering. The outer end of the lead 13 may be connected to a female snap connector (not shown) adapted to be snapped into about a male connector of the monitoring equipment. The circular cover member 14, having a downwardly extended end portion formed of an insulating plastic material, such as polyethylene or polypropylene, is fixed on the top surface of the yoke 11 by an adhesive 15.

In order to couple the terminal assembly with the base assembly which is mounted to the surface of the skin, it is sufficient only to allow the underside of the terminal assembly to come near the cylindrical chamber 1C on the top of the base assembly, whereupon the yoke 11 is attracted to the ferromagnetic element 2 and held in place thereon by the action of the magnet 12. Thus, the sensing element 3 comes into electrical contact with the lead 13 through the conductive paste (or springs) 5, the ferromagnetic element 2 and the yoke 11. Because it is not necessary to exert an external force on the base assembly upon coupling the base and terminal assemblies of the skin electrode in accordance with the invention, undesirable leaking of the electrolyte gel out of place and other inconveniences associated therewith are completely avoided and, thus, the skin electrode of the invention can be safely handled even by a non-trained person. Furthermore, the skin electrode of the invention brings about additional advantages, as noted below.

It is frequently required to monitor biopotentials of a moving patient who carries a skin electrode under his underware. For such a use, the skin electrode should desirably be as thin as possible, or otherwise it will be uncomfortable to the patient. Because of the disc-shaped configuration of both the sensing and ferromagnetic elements, the base assembly of the skin electrode in accordance with the invention can be made thinner than that of any known skin electrodes. Furthermore, the structures of the parts are very simple, so that the fabrication and assembling thereof are extremely easy and inexpensive. In addition the disc-shaped ferromagnetic element 3 provides a larger effective surface area than that of other shapes for increasing the magnetic coupling force. Furthermore, the yoke 11 of the terminal assembly is allowed to fit into the chamber 1C of the base assembly and, thus, the coupling so formed is resistive against a lateral pulling force. The cover member 14 of the terminal assembly has a diameter considerably larger than that of the case 1 of the base assembly and, thus it is easy to pick up the cover member 14 between fingers upon removal of the terminal assembly from the base assembly. Moreover, the yoke 11, which covers the upper and side surfaces of the magnet 12, protects undesirable leaking-out of the magnetic flux of the magnet 12.

Figure 3A:
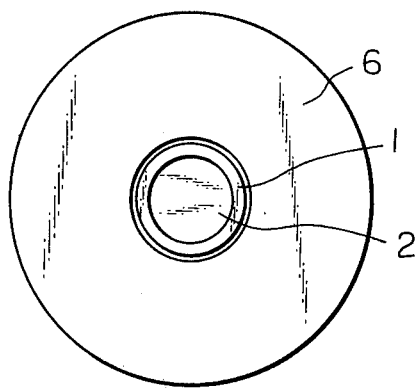
FIGS. 3(a), (b) and (c) are respectively top plan, side elevational cross-sectional and bottom plan views, illustrating another example of a base assembly of the skin electrode in accordance with the invention.
Figure 3B:
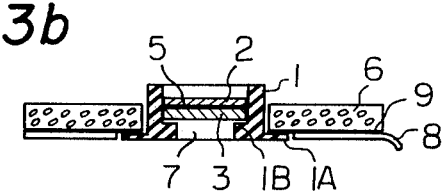
Figure 3C:
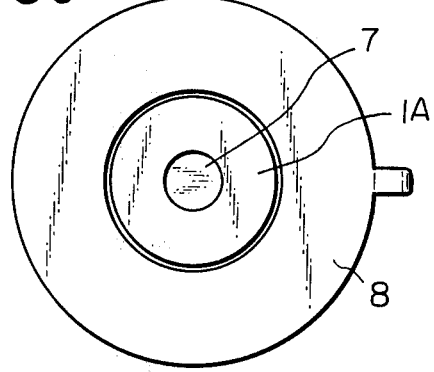

FIGS. 3(a), (b) and (c) show a modification of the base assembly shown in FIGS. 1(a), (b) and (c). Throughout these figures the same reference numericals designate like parts. The base assembly shown in FIGS. 3(a), (b) and (c) differs from that of FIGS. 1(a), (b) and (c) only in that the case 1 of the former assembly has a rim 3B at the bottom thereof. Thus, upon assembling, the sensing element 3 is first inserted into the case, in place upon the rim 3B, and then the ferromagnetic element 2 is inserted.

Figure 4A:
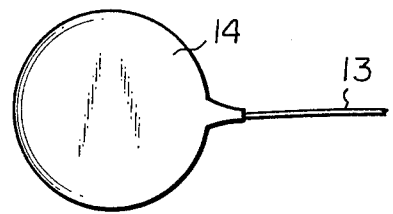
FIGS. 4(a), (b) and (c) are respectively top plan, side elevational cross-sectional and bottom plan views, illustrating another example of a terminal assembly of the skin electrode in accordance with the invention.
Figure 4B:
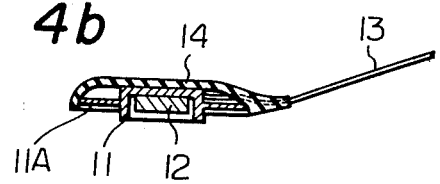
Figure 4C:
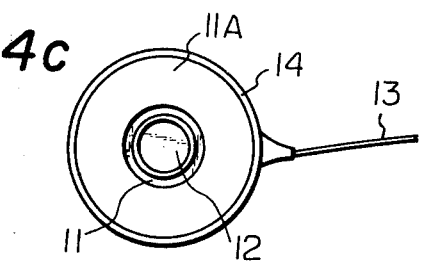

FIGS. 4(a), (b) and (c) illustrate a modification of the terminal assembly illustrated in FIGS. 2(a), (b) and (c). Throughout these figures the same reference numericals designates like parts. The terminal assembly illustrated in FIGS. 4(a), (b) and (c) differs from that of FIGS. 2(a), (b) and (c) only in that the yoke 11 of the former assembly has a flange 11A which extends perpendicularly to the axis of the yoke and is adapted to be mechanically engaged with the peripheral end portion of the circular cover member 14.

What we claim is:

1. In a skin electrode for connecting monitoring equipment to the skin of a patient comprising a base assembly mountable to the skin having a disc-shaped sensing element held in an insulating plastic case for detecting bio-potentials from the skin and transforming them into electrical signals, and a terminal assembly detachably secured to the base assembly and having a lead for connection to the monitoring equipment for transmission of the electrical signals, the improvement wherein the plastic case of the base assembly comprises a cylindrical tubular case, said base assembly further including a disc-shaped ferromagnetic element secured in said cylindrical tubular case in electrical contact with and superimposed on the sensing element with said sensing element disposed on one side of said ferromagnetic element adapted to be positioned near the skin so that a cylindrical chamber is defined by said tubular case and ferromagnetic element on the other side of the ferromagnetic element adapted to be remote from the skin, said terminal assembly comprising a disc-shaped magnet and a cylindrical yoke disposed in said chamber in magnetic attraction engagement with said ferromagnetic element, said yoke surrounding said magnet and having a depression open toward the base assembly where the magnet is held, the outer diameter of the yoke being slightly smaller than the inner diameter of the cylindrical chamber of the base assembly, said yoke being disposed in the cylindrical chamber to couple the terminal assembly to the base assembly, said lead being electrically connected to said yoke; and means for securing said tubular case to the skin with said sensing element adjacent the skin.

2. A skin electrode in accordance with claim 1, wherein said yoke is electrically conductive, said yoke having an outer cylindrical surface and a flat end surface and said lead is connected to the outer cylindrical surface of the yoke and wherein the terminal assembly includes a circular cover member adhesively fixed on said flat end surface of the cylindrical yoke.

3. A skin electrode in accordance with claim 1, wherein the terminal assembly includes a circular cover member having a peripheral end portion extended toward the sensing element, and wherein the yoke is provided with a flange which extends perpendicularly to its axis, further including means for mechanically engaging said yoke with the peripheral end portion of the circular cover member.

4. A skin electrode in accordance with claim 1, wherein said tubular case has a flange therein, the means for securing the tubular case to the skin comprises a centrally apertured disc formed of a flexible material situated upon the flange of the case with the tubular body of the case inserted into the aperture, said disc having a portion extending beyond the flange of the case, a layer of a pressure-sensitive adhesive applied to the surface adapted to face the skin of that portion of the centrally apertured disc extending beyond the flange of the case, and a removable backing strip disposed on the layer of the pressure-sensitive adhesive to protect the stickiness of the pressure-sensitive adhesive prior to use.

* * * * *